US012716087B2

(12) United States Patent
Hoffmann et al.

(10) Patent No.: US 12,716,087 B2
(45) Date of Patent: Aug. 25, 2026

(54) METHOD FOR CARRYING OUT REAL-TIME PCR

(71) Applicant: Robert Bosch GmbH, Stuttgart (DE)

(72) Inventors: Jochen Hoffmann, Renningen (DE); Tino Frank, Lucerne (CH)

(73) Assignee: Robert Bosch GmbH, Stuttgart (DE)

( * ) Notice: Subject to any disclaimer, the term of this patent is extended or adjusted under 35 U.S.C. 154(b) by 985 days.

(21) Appl. No.: 17/264,754

(22) PCT Filed: Jul. 23, 2019

(86) PCT No.: PCT/EP2019/069741
§ 371 (c)(1),
(2) Date: Jan. 29, 2021

(87) PCT Pub. No.: WO2020/025387
PCT Pub. Date: Feb. 6, 2020

(65) Prior Publication Data

US 2021/0301323 A1 Sep. 30, 2021

(30) Foreign Application Priority Data

Aug. 3, 2018 (DE) ..................... 10 2018 213 026.4

(51) Int. Cl.
*C12Q 1/6851* (2018.01)
*C12Q 1/686* (2018.01)
*G01N 35/00* (2006.01)

(52) U.S. Cl.
CPC ........... *C12Q 1/6851* (2013.01); *C12Q 1/686* (2013.01); *G01N 35/0092* (2013.01)

(58) Field of Classification Search
CPC ................. C12Q 1/686; C12Q 1/6851; C12Q 2537/143; C12Q 2561/113; B01L 7/52
See application file for complete search history.

(56) References Cited

U.S. PATENT DOCUMENTS 7,074,600 B2 * 7/2006 Dean .................... C12Q 1/6806 435/91.2
7,629,151 B2 12/2009 Gold et al.
8,119,352 B2 2/2012 Kozma et al.
9,347,096 B2 * 5/2016 Morishima .............. C12Q 1/68
2003/0148302 A1 * 8/2003 Woo
2003/0165867 A1 * 9/2003 Eyre ........................ C12Q 1/68 435/6
2014/0154787 A1 6/2014 Sun et al.
2017/0106370 A1 4/2017 Asogawa et al.

FOREIGN PATENT DOCUMENTS

CN 103347995 A 10/2013
DE 10 2006 027 675 A1 12/2007
DE 10 2010 052 524 A1 5/2012
EP 0 959 140 A2 11/1999
EP 1 138 783 A2 10/2001
EP 2671942 A1 * 12/2013 ............ C12Q 1/686
EP 3 101 144 A1 12/2016
JP 2005-516630 A 6/2005
JP 2014-23435 A 2/2014
JP 2015-107113 A 6/2015
WO 2007/059179 A1 5/2007
WO 2010/083250 A2 7/2010
WO 2012/069484 A2 5/2012
WO 2012/105176 A1 8/2012
WO WO2013177953 A1 * 12/2013 ............. C12M 1/34
WO 2014/210199 A2 12/2014
WO 2015/109330 A1 7/2015
WO 2015/151201 A1 10/2015
WO 2016/006612 A1 1/2016
WO 2016/172632 A2 10/2016

OTHER PUBLICATIONS

Applied Biosystems StepOne™Mand StepOnePlus™ Real-Time PCR Systems Standard Curve Experiment (Year: 2010).*
Stiller, M., Fulton, T.L. (2012). Multiplex PCR Amplification of Ancient DNA. In: Shapiro, B., Hofreiter, M. (eds) Ancient DNA. Methods in Molecular Biology, vol. 840. Humana Press. https://doi.org/10.1007/978-1-61779-516-9_17 (Year: 2012).*
Kang M-J, Yu H, Kim S-K, Park S-R, Yang I (2011) Quantification of Trace-Level DNA by Real-Time Whole Genome Amplification. PLoS ONE 6(12): e28661.doi:10.1371/journal.pone.0028661 (Year: 2011).*
Kang MJ, Yu H, Kim SK, Park SR, Yang I (2011) Quantification of Trace-Level DNA by Real-Time Whole Genome Amplification. PLOS ONE 6(12): e28661. https://doi.org/10.1371/journal.pone.0028661 (Year: 2011).*
Maciejewska, A., Jakubowska, J. & Pawłowski, R. Whole genome amplification of degraded and nondegraded DNA for forensic purposes. Int J Legal Med 127, 309-319 (2013). https://doi.org/10.1007/s00414-012-0764-9 (Year: 2012).*
Giardina E, et al. In silico and in vitro comparative analysis to select, validate and test SNPs for human identification. BMC Genomics. Dec. 12, 2007;8:457 (Year: 2007).*
Giardina E, et al. Whole genome amplification and real-time PCR in forensic casework. BMC Genomics. Apr. 14, 2009;10:159 (Year: 2009).*
PicoPLEX WGA Kit [Internet]. NEB; 2014 [cited Jan. 16, 2025]. Available from: https://www.neb.com/en-us/-/media/nebus/files/manuals/manuale2620.pdf (Year: 2014).*

(Continued)

*Primary Examiner* — Nancy J Leith
*Assistant Examiner* — Emma R Hoppe
(74) *Attorney, Agent, or Firm* — Maginot, Moore & Beck LLP

(57) ABSTRACT

A method for carrying out a process for an amplification of nucleic acids with sample nucleic acids and reference nucleic acids being amplified in separate reaction batches. Signals of the amplification are observed in real time. A number of amplification cycles and/or a duration of the amplification process are dynamically adjusted depending on the observed signals of the amplification.

11 Claims, 4 Drawing Sheets

(56) References Cited

OTHER PUBLICATIONS (Suzuki K, et al. Detection of Mycobacterium leprae DNA from archaeological skeletal remains in Japan using whole genome amplification and polymerase chain reaction. PLoS One. Aug. 26, 2010;5(8):e12422 (Year: 2010).*

Van der Vries E, et al. Molecular assays for quantitative and qualitative detection of influenza virus and oseltamivir resistance mutations. J Mol Diagn. May 2013;15(3):347-54. Epub Apr. 16, 2013 (Year: 2013).*

Bio-Rad Laboratories. "qPCR Analysis with CFX Maestroâ¢: Data Analysis" [Internet]. YouTube; Oct. 26, 2017. [Accessed Jan. 18, 2025] Available from: https://www.youtube.com/watch?v=UrbWOqAVmCQ (Year: 2017).*

Nolan T, Huggett J, Sanchez E, Good practice guide for the application of quantitative PCR (qPCR), LGC. 2013 (Year: 2013).*

Rao X, Lai D, Huang X. A new method for quantitative real-time polymerase chain reaction data analysis. J Comput Biol. Sep. 2013;20(9):703-11. Epub Jul. 10, 2013. (Year: 2013).*

PicoPLEX WGA Kit [online]. NEB; 2014 [retrieved on Jan. 16, 2025]. Retrieved from the Internet: https://www.neb.com/en-us/-/media/nebus/files/manuals/manuale2620.pdf (Year: 2014).*

Fehér LZ, Balázs M, Kelemen JZ, Zvara A, Németh I, Varga-Orvos Z, Puskás LG. Improved DOP-PCR-based representational whole-genome amplification using quantitative real-time PCR. Diagn Mol Pathol. Mar. 2006;15(1):43-8 (Year: 2006).*

Vet JA, et al. Multiplex detection of four pathogenic retroviruses using molecular beacons. Proc Natl Acad Sci U S A. May 25, 1999;96(11):6394-9 (Year: 1999).*

International Search Report corresponding to PCT Application No. PCT/EP2019/069741, mailed Oct. 7, 2019 German and English language document) (10 pages).

Keer, J. T., "Quantitative Real-time PCR Analysis," Essentials of Nucleic Acid Analysis: A Robust Approach, Feb. 2008, 132-166 (35 pages).

Liu, W. et al., "Validation of a quantitative method for real time PCR kinetics," Biochemical and Biophysical Research Communications, 2002, vol. 294, 347-353 (7 pages).

Liu, W. et al., "A New Quantitative Method of Real Time Reverse Transcription Polymerase Chain Reaction Assay Based on Simulation of Polymerase Chain Reaction Kinetics," Analytical Biochemistry, 2002, vol. 302, 52-59 (8 pages).

Nolan, T. et al., "Good practice guide for the application of quantitative PCR (qPCR)," LGC, Jan. 2013; retrieved from Internet: https://www.gene-quantification.de/national-measurement-system-qpcr-guide.pdf (103 pages).

Kuang, J. et al., "An overview of technical considerations when using quantitative real-time PCR analysis of gene expression in human exercise research," PLoS ONE, May 2018, vol. 13, No. 5, e0196438 (27 pages).

"qPCR guide," Eurogentec, Mar. 2009, retrieved from Internet: https://www.gene-quantification.de/eurogentec-qPCR-guide.pdf (68 pages).

"Real-time PCR handbook," Life Technologies, Jan. 2014, retrieved from Internet: https://www.thermofisher.com/content/dam/LifeTech/global/Forms/PDF/real-time-pcr-handbook.pdf (73 pages).

"Real-Time PCR Applications Guide," Bio Rad, Jan. 2006, Bulletin 5279 US/EG Rev B (105 pages).

"StepOne and StepOne Plus Real Time PCR System: StepOne Software v2.3," Jul. 2015, Applied Biosystems, Thermo Fisher Scientific, pp. 1-3 and 17-33 (22 pages).

"CFX Maestro Software User Guide," 2017, Bio-Rad, pp. 87-136 (62 pages).

Notice of Reasons for Refusal for Japanese Patent Application No. 2021-505929, Mar. 15, 2022 (8 pages).

Machine-generated English-language Translation of Notice of Reasons for Refusal for Japanese Patent Application No. 2021-505929, Mar. 15, 2022 (8 pages).

Rodrigo, A. G. et al., "Quantitation of Target Molecules from Polymerase Chain Reaction-Based Limiting Dilution Assays," AIDS Research and Human Retroviruses, 1997, vol. 13, No. 9, Mary Ann Liebert, Inc. (6 pages).

* cited by examiner

| 54 | 53 | 52 | 51 | |
|---|---|---|---|---|
| $S_3$ | $S_2$ | $S_1$ | | |
| 1 | 0 | 0 | 1 | + |
| 1 | 1 | 0 | 1 | + |
| 1 | 1 | 1 | 0 | − |
| 1 | 1 | 1 | 1 | + |

METHOD FOR CARRYING OUT REAL-TIME PCR

This application is a 35 U.S.C. § 371 National Stage Application of PCT/EP2019/069741, filed on Jul. 23, 2019, which claims the benefit of priority to Serial No. DE 10 2018 213 026.4, filed on Aug. 3, 2018 in Germany, the disclosures of which are incorporated herein by reference in their entirety.

The disclosure relates to a method for performing a real-time PCR, wherein PCR cycles are performed for amplification of sample nucleic acids and of reference nucleic acids. The disclosure further relates to a computer program which is configured for performance of the method.

BACKGROUND

The polymerase chain reaction (PCR) is a sensitive bioanalysis method for detection of particular gene segments or, in general, of nucleic acid sequences. Here, specific DNA sequences are multiplied or amplified by cyclic duplication. Multiplication requires the enzyme DNA polymerase. The products of one multiplication cycle serve as starting materials or as a model (template) for the next multiplication cycle. One known embodiment of PCR is the so-called real-time PCR, in which the reaction course can be followed especially by means of fluorescent probes. A real-time PCR allows the quantification of the starting amount of the DNA which was present in the reaction mixture before amplification. Quantification is done on the basis of reference measurements which, for each reaction, are concomitantly run and measured in separate reaction preparations in parallel.

Polymerase chain reactions proceed in multiple amplification cycles. The starting DNA is first denatured and, at the same time, separated into its individual strands (melting). In this state, primers can attach themselves to the individual strands in the next step (annealing). In the following step, the DNA polymerase attaches itself and synthesizes the respective counterstrand of the DNA in one direction, starting at the attached primers (elongation). This first amplification cycle is followed by a renewed denaturation and attachment of the primers, followed by a further synthesis of counterstrands. The reaction preparation must therefore contain DNA molecules as a model, primers, nucleotides and the enzyme DNA polymerase. Denaturation, primer hybridization and elongation are controlled via adjustment of the temperature. The PCR process is therefore generally performed in a thermocycler, with generally about 20 to 50 cycles being intended and the particular number of amplification cycles being set in advance.

German published patent application DE 10 2010 052 524 A1 describes, for example, a PCR method for qualitative and quantitative detection of nucleic acid sequences in real-time, with use of a DNA probe labeled with a fluorophore. By means of primers, what is generated under hybridization conditions is a mixture of duplexes to which the labeled primer is attached. By addition of a polymerase having exonuclease activity, the labeled DNA probe is cut and quenching is ended, thereby generating a measurable fluorescent signal.

SUMMARY

The disclosure provides a method for performing a process for amplification of nucleic acids, wherein sample nucleic acids and reference nucleic acids are preferably amplified in separate reaction preparations. According to the disclosure, signals of the amplification are observed in real-time and the number of amplification cycles and/or the duration of the amplification process are dynamically adjusted depending on signals of the amplification. For the observing of the signals of the amplification, the signals can be detected in a manner known per se, preference being given to using fluorescent probes, in order to make detectable the amplification of the nucleic acids that has taken place. In this connection, the system can be configured in such a way that the fluorescence increases proportionally with the amount of the amplified products, it being possible to use various fluorescent dyes. For example, it is possible to use DNA dyes such as cyanine dyes (e.g., SYBR® Green or PicoGreen®) or the like, which intercalate into double-stranded DNA. Another option are so-called FRET probes (Forster resonance energy transfer), wherein a donor fluorochrome interacts with an acceptor fluorochrome. The detected and evaluated signals of the amplification are set in relation to the controls, and it is on this basis that the number of amplification cycles and/or the duration of the amplification process are dynamically adjusted depending on signals of the amplification. Thus, the central point of the disclosure is that the amplification signals of sample and of reference or control are detected and evaluated in real-time or at multiple time points during the course of the process and predefined actions are carried out on the basis thereof, especially by the number of amplification cycles and/or the duration of the amplification process being dynamically adjusted.

Preferably, this process is a real-time PCR, wherein PCR cycles are performed for amplification of sample nucleic acids and of reference nucleic acids. The cycles, the number of which is dynamically adjusted, are PCR cycles in this preferred embodiment. Preferably, the signals of the amplification are related to a respectively performed PCR cycle. Thus, what can be done for example is a detection and evaluation of the signals after each PCR cycle. It is thus possible on the basis of this effectively PCR-simultaneous evaluation, for example after each cycle, to decide whether a renewed cycle is to be started or the entire PCR process is to be stopped. For example, if a signal rise is established in the case of the sample containing the sample nucleic acid and/or in the case of the preparation containing the reference nucleic acid, the PCR can be stopped. Therefore, the time for the PCR process can be shortened by being able to end the process after detection of the cycle threshold ($C_T$ value), which represents the start of the exponential rise of the amplification signal. In addition, it is thus possible to stop the PCR at a point at which a defined and known amount of PCR product has been generated. What can therefore be achieved is that, despite fluctuating PCR conditions, for example due to varying nature of the DNA-containing sample, always the same product amount is generated in the amplification.

Furthermore, the method according to the disclosure is also suitable for other amplification processes using DNA-synthesizing enzymes (amplification enzymes), for example for a whole genome amplification (WGA) or other amplification, especially also isothermal DNA amplification methods in which the amplification process proceeds essentially at a constant temperature. In the case of these processes, what can be used for example are various polymerases, helicases, ligases or combinations of enzymes of the DNA replication ensemble. In these embodiments, especially the duration of the amplification process is dynamically adjusted depending on the amplification signals.

Observing the signals of the amplification in real-time is to be understood to mean that the signals are not necessarily detected continuously, but instead that the signals can be detected at particular, time-discrete time points which are, for example, assignable to individual PCR cycles, for example after each attachment step or each elongation step of a PCR cycle.

Nucleic acid is to be understood in this connection to mean especially DNA, the DNA serving as a model (template) for amplification. Both the sample nucleic acids and the reference nucleic acids or comparative samples are concomitantly run in separate reaction preparations. Here, the reaction preparations contain the respective nucleic acid as template DNA. Furthermore, the customary reagents for, for example, a PCR preparation are present, i.e., especially primers which interact with the individual strands of the DNA at particular positions owing to the complementary nucleotide sequences and define the starting point of DNA synthesis. Furthermore, a thermostable DNA polymerase and deoxyribonucleoside triphosphates as building blocks for the DNA strand to be synthesized by the DNA polymerase are present. Furthermore, the ions necessary for the function of the DNA polymerase and a suitable buffer solution are present. For other amplification processes, especially isothermal amplification processes, for which the method is likewise advantageously usable, the reaction preparations contain relevant components which are likewise known per se.

In the method, what can be provided is that the observing and/or the evaluation of the signals of the amplification in real-time only starts when a specifiable minimum number of amplification cycles and/or a specifiable minimum duration of the amplification process has been performed. For example, this minimum cycle number can be defined as meaning that the cycle number is chosen such that no signal is to be expected before said cycle number has taken place or before the minimum duration of the amplification has elapsed. This embodiment has the advantage that capacities for observing and evaluating the signals for the phases in which no relevant results are to be expected can be saved. The minimum number of PCR cycles can, for example, lie in the range of 10 or fewer. During these initial cycles, a baseline, for example, can be generated for the subsequent evaluation.

In a preferred embodiment of the method, the process is ended when the signal intensity of the amplification in the preparation containing the sample nucleic acid reaches and/or exceeds the signal intensity of the amplification in the preparation containing the reference nucleic acid. In this case, it is to be assumed that the amount of the sample nucleic acid corresponds to the amount of the reference nucleic acids or the concentration thereof. With this embodiment of the method, especially the starting concentration of the sample nucleic acid can be ascertained, and the process can subsequently be ended. Ending the process before a specifiable maximum number of amplification cycles is reached or before a specifiable maximum duration of the process has the particular advantage that the appearance of undesired side-products is minimized, which side-products can form especially at high cycle number at the end of PCR reactions (e.g., the formation of primer dimers). This facilitates further analysis in the optional further characterization of the amplification products.

The amplification process can be terminated when optionally a maximum number of amplification cycles and/or a specifiable maximum duration of the process has been performed without a significant rise in the signal of the amplification in the preparation containing the sample nucleic acid having been established up to this time point. Said maximum number can, for example, be the number of PCR cycles that is chosen in conventional PCR experiments, for example 50 PCR cycles.

Altogether, the presently described method does not require any new assay development, since use is made of the customary reagents and reaction parameters for amplification processes. Only the control of the process, especially the dynamic intervention into the process duration and, for example, into the number of PCR cycles and optionally the composition of the controls, depending on the application case, are put into the context of a new system. At the same time, the described method allows a controlled full automation of assay workflows without having to interpose quantification methods, which would require a collection of sample with a subsequent purification of the amplification products.

The method can, for example, be carried out such that the signals of the amplification are observed in relation to respectively performed amplification cycles. The respective cycle is classified as "amplification" in the event of a significant rise in the signals. A comparison of this classification result between the preparations containing sample nucleic acids and containing reference nucleic acids for the respective cycle is used for an evaluation. As an alternative (or in addition) to individual amplification cycles, the signals can be related to definable time points during the process, the signals being captured at said definable time points. For example, the signals can be recorded at a rate between 1 s to 1 min, i.e., that, for example, the signals can be captured (e.g., by recording fluorescent images) at a cycle rate of 1 s or 30 s or 1 min and, for example, evaluated as described above. Depending on the application, the observation time window can, for example, be between 1 s and 10 min, preferably between 30 s and 5 min. In a particularly preferred embodiment of the method, the results of the amplification process are evaluated as an indicator vector display. For this purpose, amplification cycles or time points classified as "amplification" can, for example, be assigned to the indicator value "1" and the other cycles or time points to the indicator value "0".

Particularly advantageously, the starting amount of the sample nucleic acids can be ascertained and/or checked using the method. To this end, preferably at least two comparative samples having a defined, i.e., known and specified, starting amount of the reference nucleic acids are concomitantly run in parallel. For example, a comparative sample having a minimum starting amount or minimum starting concentration and at least one comparative sample having a maximum starting amount or maximum starting concentration can be used. The largest starting amount (largest standard concentration) and the smallest or minimum starting amount (smallest standard concentration) allow, then, the setting of a detection window. By means of further comparative samples having concentrations within said window, it is possible to create multiple subintervals which allow an interval assignment for the starting concentration in the sample and can, for example, be used for quality control. The various concentrations of the comparative samples or standard samples can, for example, differ by a factor of 10. Once amplification signals are establishable in the sample (indicator value of "1"), the amplification process can be terminated and the starting concentration or a concentration interval for the sample can be deduced in a comparison with the respective hitherto achieved indicator values of the preparations having the standard concentrations. A particular advantage here is that the time for performing the process can be shortened. The maximum cycle number or the maximum process duration, which has to be worked through in conventional methods, need not be performed in order to be able to detect an amplification and the quantity thereof; instead, the process can be terminated after detection of the cycle threshold ($C_T$ value), which represents the start of the exponential rise of the amplification signal. The associated time saving is particularly advantageous especially in the case of use in a point-of-care (PoC) application.

In a further preferred embodiment of the method, the method is used as an infection detection. Here, at least one comparative sample having a concentration of the nucleic acid to be detected (e.g., a characteristic gene segment of a pathogen) that represents a lower detection limit is concomitantly run. Said detection limit can be the latest termination criterion of the amplification reaction. If a signal, i.e., especially the signal "amplification", is detected earlier in the preparation containing the sample nucleic acids, the test can be rated as positive. It is possible here to concomitantly run yet further comparative samples having different concentrations of the nucleic acid to be detected, wherein, in the case of a valid test, the chronological order of the appearance of amplification signals for the comparative samples should correspond to the order of the concentrations.

In a further embodiment of the method, the method is used as a mutation detection. To this end, preferably a comparative sample having a defined concentration of the relevant nucleic acid which comprises a 100% proportion of the mutation to be detected and preferably a further comparative sample having a defined concentration of the nucleic acid which contains a 0% proportion of the mutation to be detected (wild type) are concomitantly run. Between these two limits, it is possible to choose and use multiple mixture ratios of mutation nucleic acid and wild-type nucleic acid.

In a further embodiment of the method, the method can be used for a whole genome amplification (WGA). A particular advantage here is that the amount of amplification product that forms can be checked by concomitantly running appropriate comparative reactions having nucleic acid concentrations of known concentration. Especially in the case of whole genome amplifications, what may arise is the problem of undesired side-products, especially in the case of high cycle numbers or after a relatively long amplification period, i.e., at the end of the WGA process. In contrast, the presently described method offers the advantage that the process can be terminated once a particular product amount or product concentration has been reached, meaning that the formation of undesired side-products does not occur or the formation of undesired side-products is minimized.

To use the method for a whole genome amplification, preferably at least one comparative sample containing a defined concentration of the nucleic acid (DNA) of a reference genome is concomitantly run. This first comparative sample is preferably specific for the species in question. If, for example, a human genome is to be amplified, what is used as the reference genome is the DNA of another person or preferably a mixture from a multiplicity of different persons, so that genetic diversity can be taken into account. Preferably, the defined concentration or amount of the reference genome corresponds to a maximum usable amount of DNA for whole genome amplification systems. Furthermore, a second comparative sample that contains no nucleic acid to be amplified (no template control) is preferably provided. Furthermore, a so-called quantitative reference as third comparative sample that contains a defined amount of nucleic acid of the reference genome is preferably provided, said defined amount corresponding to the desired target amount of product in the whole genome amplification. Here, this preparation of the third comparative sample contains no amplification enzyme. This means that, for said third comparative sample, no amplification takes place during the process. By using fluorescent dyes which intercalate into double-stranded DNA, which are thus independent of an amplification taking place, what occurs in the case of said third comparative sample is the intercalation of the fluorescent dye into the double-stranded DNA already present, and so the resultant fluorescent signal corresponds to the signal which is to be achieved by the process in the case of the actual sample for the whole genome amplification. The appearance of amplification signals for the comparative samples in comparison with signals for the sample defines various checkpoints which allow a controlled and automatable performance of the process.

In a further embodiment of the method, the method is used for a targeted and checked preamplification in the context of a nested PCR for example. Here, the amount of the amplified nucleic acid or the PCR products is checked and controlled by concomitantly running appropriate standards. The presently described method can also be used for a nested PCR comprising a first multiplex PCR and at least one second singleplex PCR, wherein especially the amount of the nucleic acid amplified in the first multiplex PCR can be checked using the method. In general, what occurs in a nested PCR is the amplification of multiple predefined gene segments in a first multiplex PCR. In one (or more) second singleplex PCRs, individual genes or gene segments are then specifically detected on the basis of the first PCR product. For example, said method can be used for a mutation detection, involving multiplication of the gene segments on which the mutation to be detected or the mutations potentially lie. The individual mutations are then specifically detected only in the second reaction. In this case, these second reactions in particular often have only a limited ideal working range. This means that too little or too much input material from the first PCR can adversely affect the efficiency of the reaction. With the aid of the presently described method, it is possible to measure how much sample starting material was present in the first PCR. Furthermore, the amount of the emerging amplification product or the PCR product of the first reaction can be controlled by terminating the reaction upon reaching a particular target value. On the basis of the capturable and controllable concentration of the PCR product in the preamplification, an appropriate dilution of the first PCR product can be subsequently set, and so the PCR product from the first reaction that will be used as template DNA in the second reaction can be adjusted to an optimal concentration for the subsequent detection reaction.

The described method is particularly suitable for performance in microfluidic systems, for example as a lab-on-a-chip system, with the advantage of only very low sample volumes being required. In this case, the advantages of the described system become important especially also in connection with possible automation.

The various components for performance of the described method can, for example, be provided as a kit for a user. Said kit can, then, contain especially the comparative samples, reagents, enzymes and buffers that are necessary for the process in question.

The method can be realized as a computer program which is configured for performance of the method. Said computer program can be stored on a machine-readable data carrier and/or be implemented in an appropriate controller for performance of amplification processes.

BRIEF DESCRIPTION OF THE DRAWINGS

Further features and advantages of the disclosure are apparent from the following description of exemplary embodiments in conjunction with the drawings. Here, the individual features can each be realized separately or in combination with one another.

In the drawings.

DETAILED DESCRIPTION

Figure 1:
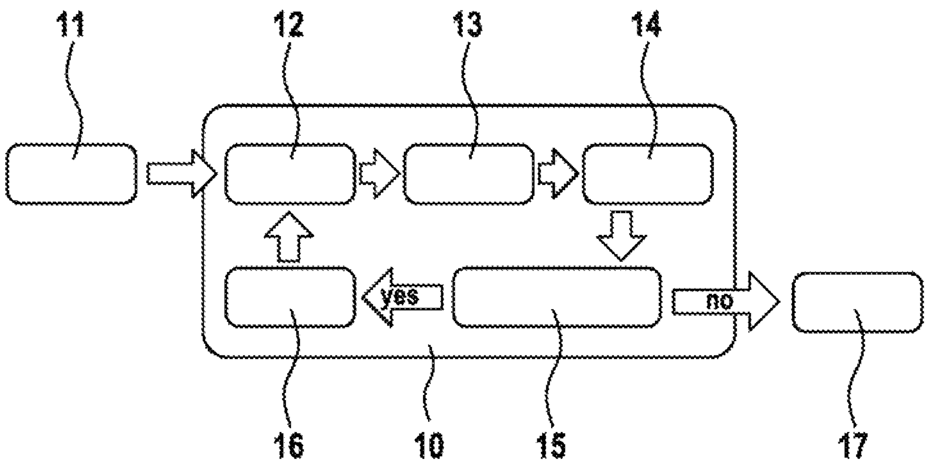
FIG. 1 shows a schematic representation of the steps of a real-time PCR with implementation of the method according to the disclosure.

FIG. 1 schematically shows the course of a real-time PCR 10 as per the method according to the disclosure. After the start 11 of the PCR process, the PCR cycles are started, these individual steps being carried out by a control of the temperature in a thermocycler. At regular intervals, especially at defined time points within the PCR cycle (or analogously at particular time points in isothermal amplification processes), signals of the amplification are captured and, for example, recorded and evaluated as fluorescent images. The choice of the respective suitable time point can, for example, depend on the probe respectively used. In the example shown here, measurement is, for example, carried out after each attachment step. However, in most cases, measurement is carried out after each elongation step. Each PCR cycle comprises the step of denaturation 12 of the template DNA. The template DNA used are sample nucleic acids and reference nucleic acids in separate reaction preparations. The denaturation step 12 is followed by the attachment (annealing) of the respective primers in step 13. In this example, this is followed by the measurement of the signals of the amplification in step 14. The measured signals are evaluated in step 15, a check in particular being made to determine whether the measured signal is classified as "amplification" or not. Especially in comparison with the reference samples, a decision is then made as to whether further PCR cycles are performed or not. For example, if it is established in step 15 that the measured signal should be classified as background, i.e., not as "amplification", the PCR cycle is continued with the elongation step 16. Thereafter, the new PCR cycle starts with the denaturation step 12. However, if it is established in step 15 that the measured signal should not be rated as background signal, but should be classified as "amplification", the PCR process can be terminated, and optionally further analyses and evaluations of the PCR products formed can be carried out (step 17).

The detection of the signals in step 14 is based on fluorescent probes, by means of which an amplification which has taken place is made detectable in various ways known per se, for example by incorporation in the DNA synthesis or by attachment or intercalation into the DNA. Especially statistical testing is then carried out to determine whether this new data point can be classified as background with data points already measured in previous PCR cycles or whether the signal significantly deviates from the hitherto determined background signal and can be referred to as "amplification".

Expediently, a minimum and a maximum PCR cycle number are specified as boundary conditions for the PCR process. The minimum cycle number defines from when a signal can be expected at the earliest. These data points are automatically assigned to the background and are not tested for amplification. Said minimum cycle number can, for example, be set to 10 or smaller. During these initial cycles, a base line can be generated. The maximum cycle number can form a termination criterion for the case of no amplification being detectable in the sample. Said number is typically the number of cycles that is also specified in a classic PCR process.

Figure 2:
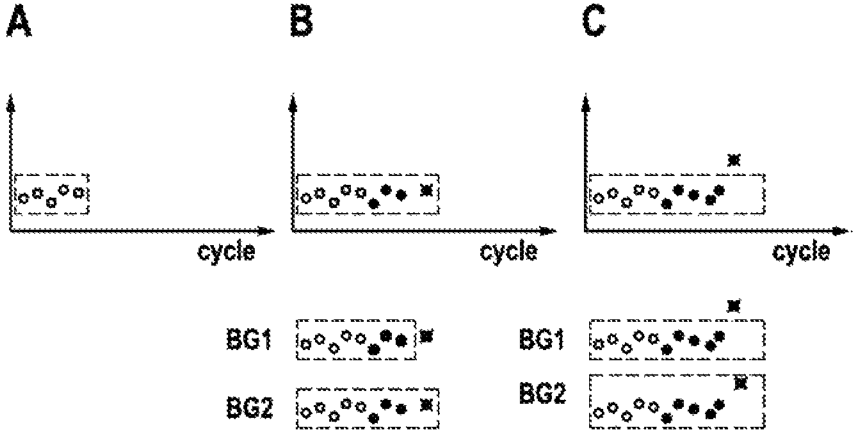
FIG. 2 show an illustration of the evaluation of fluorescent signals in a PCR process in the context of the method according to the disclosure.

FIG. 2 illustrates the evaluation (step 15 in FIG. 1) of the detected fluorescent signals. Said fluorescent signals can be captured in relation to individual PCR cycles or else in relation to particular time points during the amplification process, especially in the cases of isothermal amplification processes (e.g., in the case of whole genome amplifications). Subfigure A shows the background (BG) or a baseline that is formed by individual data points (open circles) which are measured especially in early PCR cycles and in which there can be no assumption of an amplification. The frame around the individual data points represents an estimated background with certain tolerances. This thus defined background is the basis of the tests of the subsequent data points on the basis of the measured fluorescent signals in following PCR cycles or in the following amplification process. Subfigure B depicts the subsequently measured data points as closed circles, which are based on further fluorescent signals in subsequent PCR cycles or in the subsequent process and which are located within the frame of the background. The most recent data point depicted with a cross represents the current measurement value, which is likewise located within the frame of the background. Here, it can be assumed that no amplification has taken place. What is thus initially calculated on the basis of the data points from preceding cycles is the old background, i.e., the background is ascertained for all points with the exception of the current measurement value (BG1). When the current data point is available, a second background BG2 is calculated, the current data point being included. It is then possible to carry out statistical testing to determine whether the two possible backgrounds BG1 and BG2 significantly differ. The statistical evaluation can be done as per the following specification:

Hypothesis Hl: BG1=BG2

Hypothesis H0: BG1≠BG2

If, as in subfigure B, P(H1)>P(H0), there is no significant difference and no amplification has taken place. The amplification process is continued. By contrast, if the background changes significantly owing to the current data point (P(H1) <P(H0)), an amplification can be assumed, as depicted in subfigure C. This information is the basis of further action in the amplification process and the process can be ended.

Figures 3, 4:
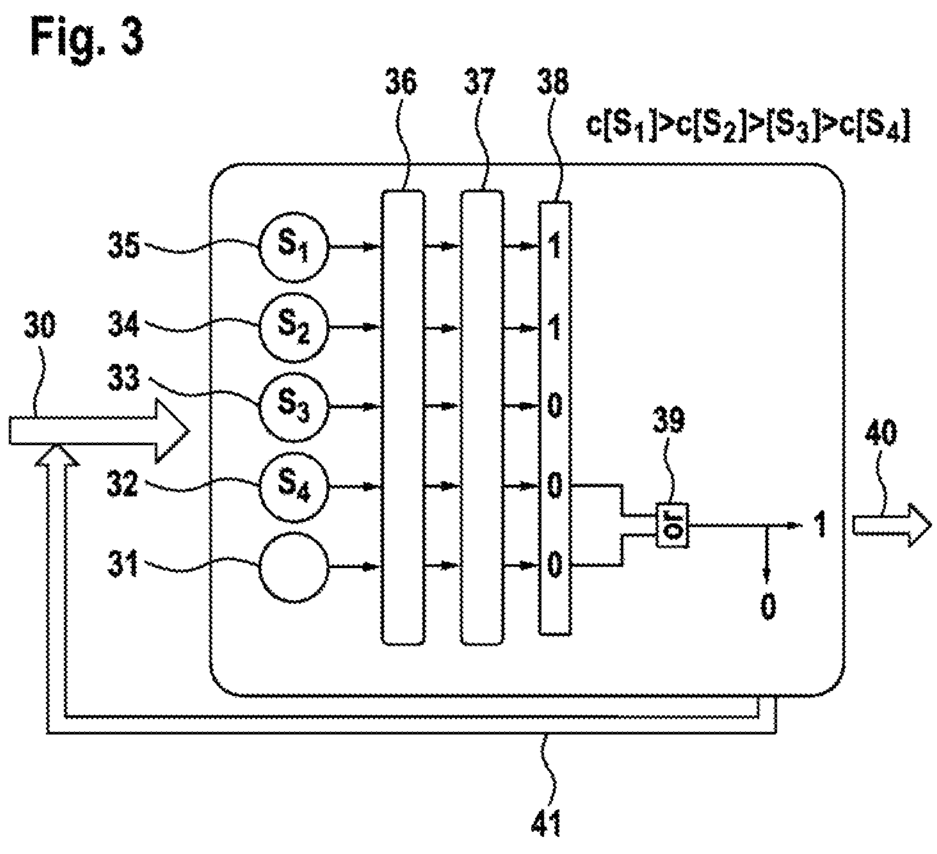
FIG. 3 show an illustration of the performance of an amplification process as per the method according to the disclosure for determination of the starting concentration of a sample.
FIG. 4 shows an evaluation of an amplification process as per the method according to the disclosure in the case of performance of an infection detection on the basis of an indicator vector display.

FIG. 3 illustrates the embodiment of the amplification process with which a starting concentration of a sample DNA is determined. This example is elucidated with reference to a PCR process. This example and the following examples can also, for example, be applied to isothermal amplification processes, wherein the observed amplification signals are then assigned not to individual PCR cycles, but to discrete time points in the amplification process. Concomitantly run in parallel with the sample 31 are various reaction preparations containing standards 32, 33, 34 and 35 as comparative samples. Here, the standard 35 represents the largest standard concentration $S_1$ and the standard 32 represents the smallest standard concentration $S_4$. Between the maximum and the minimum standard concentration, as many intermediate stages of the standard concentrations as desired can be chosen in principle. In this example, there are two concentrations $S_2$ and $S_3$. The number of different standard concentrations $S_1$ to $S_n$ determines the resolution of concentration determination. All the preparations are run in parallel after the start 30 of the PCR process and, during the individual PCR cycles, the signals of the amplification are captured in step 36. In step 37, what is evaluated is whether an amplification can be deduced or not. This can be done especially by means of the method as described in connection with FIG. 2. The numerals 1 and 0 depicted in the field 38 stand for a classification as amplification ("1") or no amplification ("0"). The PCR process can be terminated when an amplification is established for the sample 31. In comparison with the amplification results for the standard samples 32 to 35, it is then possible to deduce the concentration interval in which the starting concentration of the DNA in the sample 31 was present. If no amplification could be established for the sample 31, but an amplification already appeared for the lowest standard concentration 35, the PCR process can likewise be terminated, since the starting concentration in the sample 31 is below the detection limit which is defined by the minimum standard concentration 35. This approach is realized by the query 39, by a check being made between the sample 31 and the comparative sample 32 or the standard having the lowest concentration to determine whether an amplification was established for one of the two preparations. In this case, the PCR process is ended (step 40). If an amplification cannot be established either for the sample 31 or for the standard S4 having the lowest concentration 32, the next PCR cycle is carried out in step 41. This method allows an unambiguous assignment of a concentration interval. The concentration intervals are, then, defined by the number of standards.

What is to be expected here is that the standards $S_1$ to $S_n$ provide amplification signals successively from the greatest concentration up to the lowest concentration as the PCR process advances. If an amplification is established for the sample 31, and at the same time an amplification for the standards $S_1$ to $S_i$ ($i<n$), the starting concentration for the sample 31 lies in the interval $[S_i, S_{i+1}]$. If the establishment of an amplification for the standards is not in agreement with the order of their concentrations, the test is not valid.

Thus, if one preparation having a lower standard concentration shows an amplification at a PCR cycle at which a standard having a higher concentration does not yet show any amplification, the reactions are not equally efficient or not comparable. The choice of the standard concentrations can, for example, be made such that they each differ from one another by a factor of 10. This corresponds to a quantification in the context of a classic real-time PCR.

FIG. 4 illustrates the method by means of an indicator vector display for an infection detection. In addition to the actual sample 51, three standards 52, 53, 54 are concomitantly run, wherein the standard 52 is the standard $S_1$ having the lowest concentration of the DNA to be detected, the standard 53 is the standard $S_2$ having a medium concentration of the DNA to be detected and the standard 54 is the standard $S_3$ having a maximum amount of the DNA to be detected. The standard $S_1$ represents the detection limit. Said detection limit is the latest termination criterion of the reaction. If an amplification is established earlier for the sample 51 and if the order of the appearance of the amplification for the standards corresponds to the order of their concentration, the test is rated as positive. FIG. 4 summarizes, in an indicator vector I, the evaluations to determine whether the reaction can be rated as amplification or not at a particular PCR cycle. In said vector, each reaction vessel or each PCR preparation (samples and standards) has an entry which is re-evaluated after each cycle. A reaction is rated as "amplification" if a signal is detectable above the background. The indicator value 1 (true) is assigned thereto in the indicator vector I. If no amplification is establishable, the indicator of the reaction is set to 0 (false). In this example, the standard $S_3$ is the largest standard and is listed on the left as upper detection limit. The second standard $S_2$, which in terms of amount is between the largest and the smallest standard, follows next. Following at the third position is the smallest standard $S_1$, which represents the detection limit. Following as the last entry in the state vector is the actual sample 51. The experiment is initialized with I=[0,0,0,0]. FIG. 4 shows the four vectors which represent a valid test. All twelve other possible cases are not permissible, and the test would have to be reported as invalid. In the case of I=[1,1,1,0], the signal is in the range of the detection limit. In this case, one or more cycles can optionally be attached owing to noise of reaction efficiency, so that any small differences present between the individual reaction vessels do not lead to an error in the test decision. In the last column of the display, the test result is displayed as positive (+) or as negative (−) for the respective vectors. Once one of these vectors is present, the reaction can be terminated.

Figure 5:
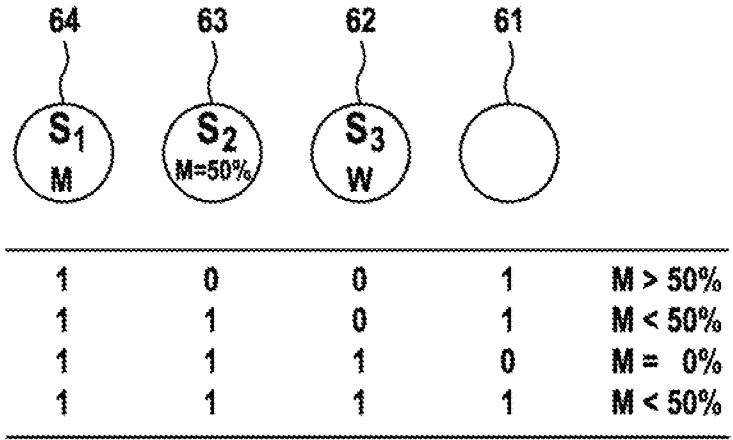
FIG. 5 shows an evaluation of an amplification process as per the method according to the disclosure in the case of performance of a mutation detection on the basis of an indicator vector display.

FIG. 5 illustrates the embodiment of the method for application of a mutation detection, likewise as an indicator vector display. In the case of a mutation detection, what is generally used is a predefined amount of the sample DNA in the sample 61 to be tested. Since the amount is predefined, the same amount of standard DNA or reference DNA is always used in the standards 62, 63 and 64. The standard $S_1$ 64 contains an initially charged template DNA in which 100% has the mutation (M) to be detected. Said standard $S_1$ forms the upper limit at which an amplification should be detected first. The lower limit and hence the last termination criterion of the reaction is a standard $S_3$ 62 which contains 100% wild-type template (W). Between these two limits, it is possible, then, to choose multiple mixture ratios of mutation DNA and wild-type DNA. In this example, a further standard $S_2$ 63 is provided that contains 50% mutation (M=50%). The setting of mixture ratios of mutation DNA and wild-type DNA allows the division of the sample into proportion bins, analogous to histograms. The standard $S_2$ with M=50% that is chosen here allows a categorization of the proportion of mutation of greater than 50% and less than 50%. In this approach, it is thus, for example, possible to determine the ploidity of the gene. Finer subdivisions are achieved by the insertion of further standards and by a numerical estimation of the efficiency. As elucidated in the previous example with reference to FIG. 4, the reaction is checked via the state vector I and test decisions are accordingly made.

Figure 6:
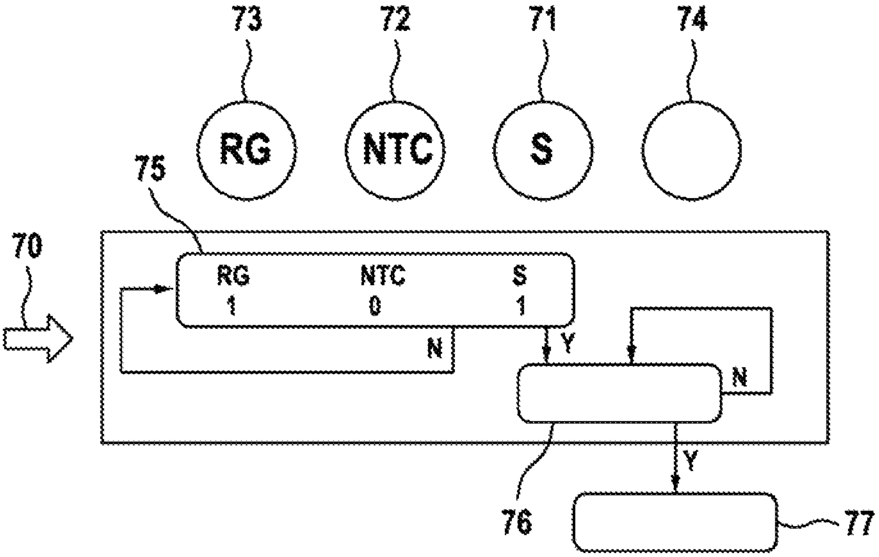
FIG. 6 show an illustration of the course of the method according to the disclosure in the case of a whole genome amplification and FIG. 7 shows a schematic overview of the necessary instrument components for performance of a real-time PCR as per the method according to the disclosure.

FIG. 6 illustrates the method in connection with a whole genome amplification. In the case of a whole genome amplification, all sequences which occur in a sample are amplified, i.e., not just defined DNA sequences which are addressed via primers. In a classic whole genome amplification, fluorescent probes, as is customary in a real-time PCR, are not used; instead, the amplification product which forms is visualized and quantified by the use of specific dyes. Said specific dyes (e.g., PicoGreen®, SYBR® Green) intercalate into double-stranded DNA and, in doing so, emit light more intensely, meaning that a rise in fluorescence indicates an amplification that has taken place. Thus, if a fluorescent signal is detectable, this indicates the presence of double-stranded DNA, and so this can thus be rated as amplification. Said dye is added in a defined amount to the reaction mixtures in the preparations for the process. Besides the actual sample 71 (S), three further comparative samples 72, 73 and 74 are concomitantly run in the process for the whole genome amplification. The comparative sample 72 contains no template DNA as so-called no template control (NTC). In the case of said sample, no amplification should be establishable, since DNA to be amplified is not present. As further comparative sample 73, the DNA of a reference genome (RG) is concomitantly run. Said reference genome is expediently species-specific. For example, if a human genome is to be amplified as a whole, the genome of one or more other persons is used as reference genome. The amount used of the reference genome corresponds, for example, to the maximum usable amount for a suitable whole genome amplification system. Said reference genome in the comparative sample 73 should therefore provide an amplification signal first of all. After the start 70, the reaction is performed and is tested for amplification until the reference genome 73 and the sample 71 are positive in the state vector (state 75). Thus, in the state 75, both reference genome 73 and sample 71 show an amplification and the NTC control 72 shows no reaction or amplification. It is only in this state that sufficient DNA is present in the sample, and up to this state, no nonspecific primer amplification (formation of primer dimers) has taken place, as has been shown on the basis of the control 72. This state represents a first checkpoint. If the conditions for the first checkpoint have been met, the reaction is continued, but now tested for a new termination criterion 76. The new test criterion 76 is the comparison of the intensity of the amplification for the sample 71 and the quantitative reference 74. Said quantitative reference 74 contains the desired amount of reference genome, this corresponding to the desired amount of product in the whole genome amplification. Here, the quantitative reference 74 contains all the components in the WGA preparation, like the other preparations, with the exception of the amplification enzyme. As a result, no amplification, i.e., no DNA synthesis, takes place in the quantitative reference 74 during the reaction. What is provided is only a reference fluorescent signal due to the initially charged fluorescent dye. If, then, amplified sample 71 and the quantitative reference 74 have the same fluorescence intensity, it can be assumed that the same amount of double-stranded DNA is present in principle in both preparations, and so the reaction can be terminated in step 77. As a further termination criterion, what can be provided is that the NTC control 72 shows an amplification signal.

This method can also be applied to a specific, targeted preamplification in which the amount of DNA that is synthesized in a preamplification is checked. In this case, specific primers are used instead of the whole genome, the result being that specific gene segments are accordingly highly copied. What can also be used here as probe instead of a dye which intercalates at double-stranded DNA is a specific fluorescently labeled probe which generates a fluorescent signal depending on synthesized DNA, for example a TaqMan® probe with fluorophore and quencher. The quantitative reference then contains the desired target amount of amplified material, an equivalent amount of cleaved probe, i.e., the same amount of free fluorophores and quenchers, and a complementary residual amount of the probe. The basis of this is that, in the case of a real-time PCR preparation in a TaqMan® probe system, a defined starting amount of the probes ($N_0=c_0V$) is specified. When the amplification starts, the probe is cleaved. The amount of probes and free fluorophores is then dependent on the copy number $N_{Amplicon}$ that arises. The residual probes $N_s$ can be calculated using $N_s=N_0-N_{Amplicon}$. Instead of an NTC control, what is concomitantly run as termination criterion is a further reference which makes a detection limit for the amplification (LoA—limit of amplification) detectable. Here, a minimum genome dilution to be used is used. Here, the first checkpoint is thus the amplification time point at which an assay-specific, predefined genome dilution, i.e., the reference LoA, was amplified.

The methods of the whole genome amplification as per the explanations in relation to FIG. 6 and the mutation detection as per the explanations in relation to FIG. 5 can be linked to one another and be configured as a monitored workflow for a mutation detection. Here, microfluidic systems and/or pipetting robots can be used. Such a fully automatic workflow can, especially in connection with microfluidic systems, offer a very advantageous possible use of the method according to the disclosure which can, for example, be used in point-of-care applications.

Figure 7:
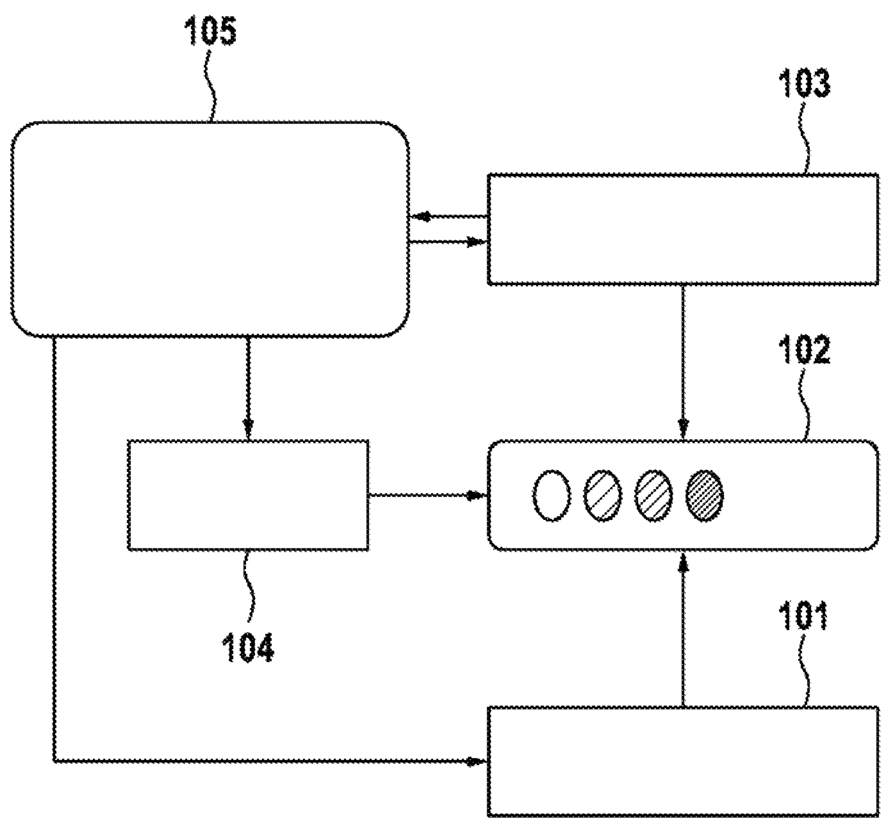

FIG. 7 illustrates the instrument components which can be used for the described real-time PCR processes. Here, the basis is formed by an instrument which makes an optofluidic real-time PCR possible and thus allows a signal readout of optical signals in order to be able to observe the amplification in the individual samples or PCR reactions on the basis of fluorescence signals. Such an instrument comprises a heating and cooling system 101 (thermocycler) which interacts with the various PCR reaction preparations 102. Furthermore, the instrument has an optical unit 103 which effects the readout of the amplification signals. Furthermore, a device for fluid handling 104 can be provided, for example a robot system or a corresponding microfluidic system. Altogether, it is advantageous to configure such a system as a microfluidic system, since a microfluidic system can be operated with very small sample volumes and allows semi-automation or full automation. The system is furthermore provided with a reaction control unit 105 which effects an in situ evaluation of the optical data. To realize the feedback real-time PCR system of the present disclosure, the reaction control unit 105 is configured such that it can interact with all units of the system. The reaction control unit 105 can especially control the dynamic adjustment of the number of PCR cycles depending on the observed signals of the amplification.

The invention claimed is:

1. A method for performing an amplification process for amplification of nucleic acids, comprising:

amplifying sample nucleic acids and reference nucleic acids in separate reaction preparations, the amplifying including amplifying a whole genome and concomitantly running at least one first comparative sample having a defined concentration of nucleic acid of a reference genome;

detecting signals corresponding to the amplification in real-time; and during the amplification process, automatically adjusting, with a control unit, a number of amplification cycles and/or a duration of the amplification process based on the detected signals, wherein the detected signals corresponding to the amplification are based on detection of light emitted by fluorescent dyes intercalated into double-stranded DNA, wherein the automatic adjusting further comprises:

identifying a first checkpoint when the detected signals indicate amplification of both the sample nucleic acids and the reference genome in the at least one first comparative sample; and after the identifying of the first checkpoint:

comparing intensity of the sample nucleic acids and a second comparative sample comprising a quantitative reference that contains a desired amount of product in the whole genome application and no amplification enzyme; and terminating the amplifying of the sample nucleic acids and reference nucleic acids in response to the intensity of the sample nucleic acids and the quantitative reference being equal.

2. The method as claimed in claim 1, wherein:

the amplification of the sample and the reference nucleic acids is performed in a context of a real-time polymerase chain reaction (PCR), and the amplification cycles are PCR cycles.

3. The method as claimed in claim 1, wherein:

the detecting of the signals of the amplification in real-time starts when a specifiable minimum number of the amplification cycles and/or a specifiable minimum duration of the amplification process has been performed.

4. The method as claimed in claim 1, wherein:

the signals of the amplification are detected in relation to respectively performed amplification cycles and/or in relation to definable time points, the signals of the amplification are classified as "amplification" in an event of a statistically significant rise in the signals of the respective cycle or a respective time point, and a comparison of a result of the classification as "amplification" or not is used for an evaluation.

5. The method as claimed in claim 4, further comprising:

evaluating results of the process for amplification as an indicator vector display, wherein the amplification cycles or time points classified as "amplification" are assigned to an indicator vector of the indicator vector display as a value of "1" and the other amplification cycles or time points are assigned to the indicator vector as a value of "0".

6. The method as claimed in claim 1, further comprising:

ascertaining and/or checking a starting amount of the sample nucleic acids, wherein at least two comparative samples having a defined starting amount of the reference nucleic acids are concomitantly run in parallel.

7. The method as claimed in claim 1, further comprising:

detecting an infection based on the amplifying, wherein at least one comparative sample having a concentration of a nucleic acid to be detected that represents a lower detection limit for the infection detection is concomitantly run in parallel.

8. The method as claimed in claim 1, further comprising:

detecting a mutation based on the amplification, wherein a comparative sample having a defined concentration of nucleic acid having a 100% proportion of the mutation to be detected and a comparative sample having a defined concentration of nucleic acid which contains a 0% proportion of the mutation to be detected are concomitantly run.

9. The method as claimed in claim 1, wherein:

the process for amplification is a nested PCR comprising a first multiplex PCR and at least one second singleplex PCR, and an amount of nucleic acid amplified in the first multiplex PCR is checked.

10. The method as claimed in claim 1, wherein the method is performed by a computer program.

11. The method of claim 1, wherein the defined concentration corresponds to a maximum usable amount of nucleic acid for whole genome amplification systems.

* * * * *